United States Patent [19]

Minowa et al.

[11] Patent Number: 4,499,027

[45] Date of Patent: Feb. 12, 1985

[54] PROCESS FOR PREPARING OPTICALLY ACTIVE [(3-AMINO-3-CARBOXY)PROPYL-1]PHOSPHINIC ACID DERIVATIVES

[75] Inventors: Nobuto Minowa, Yokohama; Shunzo Fukatsu; Kunitaka Tachibana, both of Tokyo; Taro Niida, Yokohama; Sadaaki Mase, Tokyo, all of Japan

[73] Assignee: Meiji Seika Kaisha, Ltd., Tokyo, Japan

[21] Appl. No.: 611,686

[22] Filed: May 18, 1984

[30] Foreign Application Priority Data

May 27, 1983 [JP] Japan .................................. 58-92448

[51] Int. Cl.$^3$ ............................................... C07F 9/30
[52] U.S. Cl. .............................. 260/502.5 G; 260/941; 260/971; 71/86
[58] Field of Search ................................ 260/502.5 G

[56] References Cited

U.S. PATENT DOCUMENTS 4,226,610 10/1980 Takematsu et al. ......... 260/502.5 G

FOREIGN PATENT DOCUMENTS 0085391 8/1983 European Pat. Off. ..... 260/502.5 G
2031896 4/1980 United Kingdom ........ 260/502.5 G Primary Examiner—J. E. Evans
Attorney, Agent, or Firm—Frishauf, Holtz, Goodman & Woodward

[57] ABSTRACT

Disclosed is a novel process for optically active [(3-amino-3-carboxy)propyl-1]phosphinic acid derivatives, which comprises reacting a Shiff's base with a derivative of vinylphosphinate in the presence of a base, and subjecting the resulting compound to hydrolysis to form the optically active [(3-amino-3-carboxy)propyl-1]phosphinic acid derivatives as either [L-(3-amino-3-carboxy)propyl-1]phosphinic acid derivatives or [D-(3-amino-3-carboxy)propyl-1]phosphinic acid derivatives.

16 Claims, No Drawings

PROCESS FOR PREPARING OPTICALLY ACTIVE [(3-AMINO-3-CARBOXY)PROPYL-1]PHOSPHINIC ACID DERIVATIVES

BACKGROUND OF THE INVENTION

This invention relates to a novel process for preparing optically active [(3-amino-3-carboxy)propyl-1]phosphinic acid derivatives. More particularly, it relates to a process for preparing optically active [(3-amino-3-carboxy)propyl-1]phosphinic acid derivatives which themselves are useful as herbicides and antifungal agents, or as starting materials for herbicides and antifungal agents.

It has been known that [L-(3-amino-3-carboxy)propyl-1]methylphosphinic acid has herbicidal activity about twice as strong as [DL-(3-amino-3-carboxy)propyl-1]methylphosphinic acid and, of the compound, the herbicidal activity of L-form is stronger D-form (see U.S. Pat. No. 4,265,654 and the Experiment in this specification). Therefore, there has been desired a method effective for selectively producing [L-(3-amino-3-carboxy)propyl-1]methylphosphinic acid only.

Conventionally, in the preparation of [L-(3-amino-3-carboxy)propyl-1]methylphosphinic acid, there have been known a method in which SF-1293 substance (U.S. Pat. No. 3,832,394 or Helv. Chim. Acta., 55, 224 (1972)) is decomposed with an acid (Helv. Chim. Acta., 55, 224 (1972)), a method in which SF-1293 substance is decomposed with a microbial enzyme (Japanese Unexamined Patent Publication No. 31890/1974) and a method in which the product is optically separated into D-form and L-form by the use of a microbial enzyme (U.S. Pat. No. 4,226,941). These methods, however, involves certain problems such as high production cost and difficulty in industrial application on a large scale.

The present inventors have made intensive studies to solve the above-mentioned problems, and succeeded in an asymmetric synthesis of the aimed compounds of this invention by subjecting a Shiff's base (a compound of the general formula (I)-1 or (I)-2 below) which is inexpensively available from glycine or its ester and an optically active ketone, to Michael reaction with an ester of vinyl phosphinic acid (a compound of the general formula (II) below) in the presence of a base, and as a result, have found a superior process for selectively synthesizing optically active [(3-amino-3-carboxy)propyl-1]phosphinic acid derivatives (a compound of the formula (III) below), in which a product either rich in L-form or rich in D-form of the [(3-amino-3-carboxy)propyl-1]phosphinic acid derivatives can be formed by selectively using the compound of the formula (I)-1 or that of the formula (I)-2. They have also found that the formation of the product either rich in L-form or rich in D-form by use of the compound of the formula (I)-1 or the compound of the formula (I)-2 can be regulated or controlled by selecting the reaction temperature.

Accordingly, an object of this invention is to provide an industrially superior process for selectively producing optically active [(3-amino-3-carboxy)propyl-1]phosphinic acid derivatives.

Another object of this invention is to provide a process for producing optically active [(3-amino-3-carboxy)propyl-1]phosphinic acid derivatives regulatively as a product either rich in L-form or rich in D-form.

According to this invention, there is provided a process for preparing optically active [(3-amino-3-carboxy)propyl-1]phosphinic acid derivatives, which comprises reacting a compound represented by the formula (I)-1:

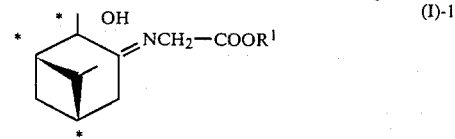

wherein $R^1$ represents a straight or branched chain alkyl group having 1 to 5 carbon atoms, an aryl group or an aralkyl group; and the absolute configurations of the three asymmetric carbon atoms indicated by * are each S-form or a compound represented by the formula (I)-2:

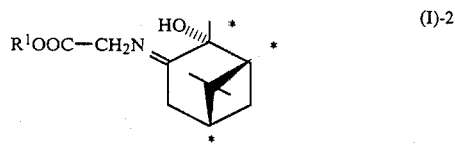

wherein $R^1$ have the same meaning as defined above; and the absolute configurations of the three asymmetric carbon atoms indicated by * are each R-form with a compound represented by the formula (II):

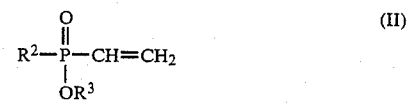

wherein $R^2$ and $R^3$ may be the same or different and each represent a straight or branched chain alkyl group having 1 to 5 carbon atoms, an aryl group or an aralkyl group, in the presence of a base, and subjecting the resulting compound to hydrolysis to form the optically active [(3-amino-3-carboxy)propyl-1]phosphinic acid derivatives represeted by the formula (III) as a product either rich in L-form or rich in D-form:

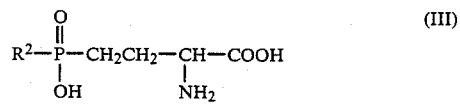

wherein $R^2$ have the same meaning as defined above; and the absolute configuration of the amino acid is L-form or D-form, or, more specifically, to form the optically active [(3-amino-3-carboxy)propyl-1]phosphinic acid derivatives represented by the above formula (III) as a product either rich in an [L-(3-amino-3-carboxy)propyl-1]phosphinic acid derivative represented by the formula (III)-1:

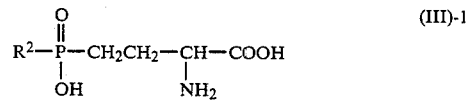

wherein $R^2$ have the same meaning as defined above; and the absolute configuration of the amino acid is L-form or rich in a [D-(3-amino-3-carboxy)propyl-1]phosphinic acid derivative represented by the formula (III)-2:

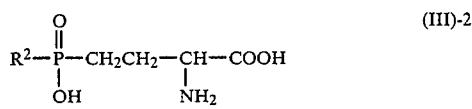

wherein $R^2$ have the same meaning as defined above; and the absolute configuration of the amino acid is D-form.

DESCRIPTION OF THE PREFERRED EMBODIMENTS

In the above formula (I)-1 or (I)-2, the alkyl group having 1 to 5 carbon atoms represented by $R^1$ includes a methyl, ethyl, propyl, butyl and t-butyl. The aryl group includes, for example, a phenyl, chlorophenyl, nitrophenyl and methoxyphenyl. The aralkyl group includes, for example, a benzyl.

In the above formula (II), the straight or branched chain alkyl group having from 1 to 5 carbon atoms represented by $R^2$ and $R^3$ includes, for example, a methyl, ethyl, propyl, isopropyl, butyl and t-butyl. The aryl group includes, for example, a phenyl, chlorophenyl, nitrophenyl and methoxyphenyl. The aralkyl group includes, for example, a benzyl.

The compound represented by the formula (I)-1 or (I)-2 can be prepared according to the method disclosed in Chem. Pharm. Bull., 26 (3), 803–808 (1978).

The compound represented by the formula (II) can be prepared according to the method disclosed in European Patent Publication No. 0 085 391 of Aug. 10, 1983.

In the present reactions, both the compound (I)-1 or (I)-2 and the compound (II) are first reacted in the presence of a base. As the base, there may be used, for example, n-butyl lithium, sec-butyl lithium, t-butyl lithium, lithium diisopropylamide, lithium isopropylcyclohexylamide, lithium di(trimethylsilyl)amide, sodium methylate, sodium ethylate, sodium hydride, potassium t-butoxide, calcium diisopropylamide, methylmagnesium chloride, methylmagnesium bromide and methylmagnesium iodide.

The above reaction is usually carried out in an organic solvent. In this case, the organic solvent includes, for example, methanol, ethanol, toluene, dimethoxyethane, dimethylsulfoxide, tetrahydrofuran, diethyl ether, hexamethylphosphoric triamide and dioxane.

According to this invention, it is possible to produce the aimed product either rich in L-form or rich in D-form by using either of the starting compounds of the formula (I)-1 and (I)-2, and also possible to regulate or control the formation of the aimed product either rich in L-form or rich in D-form by selecting the reaction temperature while using the compound (I)-1 or the compound (I)-2.

The temperature at which the above reaction is carried out may range from $-100°$ to $25°$ C. More specifically speaking, when the compound (I)-1 (absolute configuration=S) is used under the temperature condition ranging from $-100°$ to $25°$ C., it is possible to obtain a product either rich in L-form or rich in D-form. In particular, when the compound (I)-1 is used under the temperature condition of $-100°$ to $-75°$ C., it is possible to produce the product rich in L-form, and under the temperature condition of $-60$ to 25, the product rich in D-form.

Similarly, when the compound (I)-2 (absolute configuration=R) is used under the temperature condition ranging from $-100°$ to $25°$ C., it is possible to obtain a product either rich in D-form or rich in L-form. In particular, when the compound (I)-2 is used under the temperature condition of $-100°$ to $-75°$ C., it is possible to produce the product rich in D-form, and under the temperature condition of $-60$ to 25, the product rich in L-form.

The above reaction of the compound (I)-1 or (I)-2 with the compound (II) may be carried out for 0.5 to 24 hours to complete it. The compound (II) may be used in 1 to 2 moles per mole of the compound (I), whereas the base may be used in 1 to 3 equivalent weights, based on one equivalent weight of the compound (I). The amount of solvent may be selected within the range usually used for this purpose, namely, 1 to 10 lit. per mole of the compound (I)-1 or (I)-2.

Thus, there is produced an intermediate product rich in a compound represented by the formula (III)'-1:

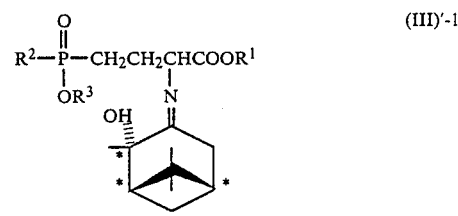

or rich in the formula (III)'-2

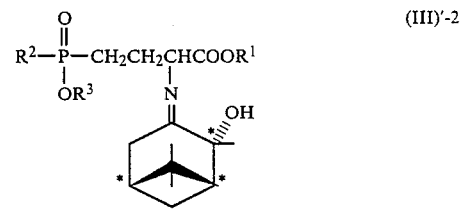

wherein $R^1$, $R^2$ and $R^3$ have the same meanings as defined above; and the absolute configurations of three asymmetric carbon atoms indicated by * are each S-form or R-form, respectively, which may be transformed, without isolation, to the compound (III) by means of a conventional deprotecting method such as hydrolysis. Namely, a mineral acid such as hydrochloric acid or sulfuric acid may be added to the reaction mixture containing the compound (III)', followed by heating of the mixture. Alternatively, the solvent may be distilled off from the reaction mixture and thereafter the compound (III)' may be extracted with a water—organic solvent system (methylene chloride, chloroform, ethyl acetate, toluene and diethyl ether are exemplified as the organic solvent), then the extract or the concentrated extract may be heated with a mineral acid to give the compound (III).

The mineral acid may be employed in large exess, for example, in an amount of 30 molar times the compound (III)'. The temperature at which the reaction is carried out may range from $20°$ to $150°$ C. The reaction time may be within the range of from 0.5 to 24 hours.

(1S,2S,5S)-2-hydroxypinane-3-one or (1R,2R,5R)-2-hydroxypinane-3-one can be recovered by treating the compound (III)' with an acid, for example, an aqueous citric acid or diluted hydrochloric acid.

After completion of the reaction, the compound (III) can be isolated by neutralization and purification in a conventional method. Where the product is to be further purified, it may be performed, for example, by chromatography using a strongly acidic ion-exchange resin or by recrystallization from a solvent such as a water-alcohol system (methanol, ethanol, propyl alcohol, isopropyl alcohol, n-butanol and t-butanol may be exemplified as the alcohol).

The compound (III), if desired, may be derived to its salt, such as sodium, potassium or ammonium salt. Further, it may be derived to its acid-addition salt such as hydrochloric acid and sulfuric acid.

The optically active [(3-amino-3-carboxy)propyl-1]phosphinic acid derivatives represented by the formula (III) may include, for example, L-form and D-form of [(3-amino-3-carboxy)propyl-1]methylphosphinic acid, [(3-amino-3-carboxy)propyl-1]ethylphosphinic acid and [(3-amino-3-carboxy)propyl-1]phenylphosphinic acid, respectively.

[L-(3-amino-3-carboxy)propyl-1]methylphosphinic acid that is one of the compounds of formula (III), is useful as a herbicide. The compound (III) is also useful as an additive to a culture medium, when preparing the SF-1293 substance which is useful as a herbicide.

As described above, the process of the invention comprises reacting the Schiff's base (I)-1 or (I)-2 with the compound (II) in the presence of a base, and subject the resulting product (III)' to hydrolysis to give selectively the optically active [(3-amino-3-carboxy)propyl-1]phosphinic acid derivative (III). Thus, the present process is a very superior industrial method for producing the compound (III), in a low cost, in a small number of steps, in a high yield, with high selectivity and on a large scale, as compared with the prior art processes for preparing the optically active compound (III).

This invention will be described in greater detail by the following examples, which, however, should not be construed to limit the scope of the invention.

REFERENTIAL EXAMPLE 1

Relationship between the reaction temperature and the formation of L-rich or D-rich product The compound (I)-1 ($R^1$=ethyl, absolute configuration=S) was reacted with the compound (II) ($R^2$=$CH_3$ and $R^3$=$OCH_3$) under the conditions shown in Table 1 below to give the compound (III) ($R^2$=$CH_3$) either rich in L-form or rich in D-form as shown also in Table 1.

TABLE 1

| Test No. | Michael reaction Donor | Acceptor | Solvent | Temp. (°C.) | (III) Yield (%) | $[\alpha]_D$ (c = 1.0, $H_2O$) |
|---|---|---|---|---|---|---|
| 1 | (I)-1 | (II) | THF | 20 | 15 | −10.0° (D) |
| 2 | " | " | " | 10 | 23 | −11.8° (D) |
| 3 | " | " | " | 0 | 24 | −11.7° (D) |
| 4 | " | " | " | −10 | 31 | −8.6° (D) |
| 5 | " | " | " | −20 | 43 | −11.5° (D) |
| 6 | " | " | " | −35 | 66 | −8.0° (D) |
| 7 | " | " | " | −50 | 46 | −6.8° (D) |
| 8 | " | " | " | −60 | 49 | −4.8° (D) |
| 9 | " | " | " | −78 | 66 | +13.4° (L) |
| 10 | " | 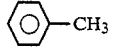 | | 0 | 23 | −9.0° (D) |
| 11 | " | " | " | −78 | 56 | +10.1° (L) |

Donor: 1.0 eq.,
Base: t-BuOK, 2.0 eq.
Acceptor: 1.0 eq.,
Solvent: 4% concentration
Hydrolysis: 6N HCl, 110° C., 20 hrs.

EXAMPLE 1

Synthesis of [L-(3-amino-3-carboxy)propyl-1]methylphosphinic acid

In 6 ml of tetrahydrofuran, 354 mg of potassium t-butoxide was dissolved under nitrogen stream and then the solution thus obtained was cooled to −78° C. To the solution, 400 mg of the compound (I)-1 ($R^1$=ethyl; absolute configuration=S) and further 190 mg of methyl ester of methyl vinylphosphinic acid were added. The resulting reaction mixture was stirred at −78° C. for 30 minutes and 4 ml of 1N HCl were added thereto, followed by concentration. To the thus obtained residue, 4 ml of 6N HCl was added and then the mixture was stirred under reflux for 20 hours. The reaction mixture was concentrated and 5 ml of propyleneoxide was added, followed by further stirring for 1 hour. After completion of stirring, the reaction mixture was concentrated and the crude product thus obtained was purified by use of an ion-exchange resin Dowex 50×2 (trade name, produced by Dow Chemical Co.) to give 188 mg (yield 66%) of crystalline powder of the desired product having a specific rotation of $[\alpha]_D$+13.4° (c=1.0, $H_2O$) and melting at 227° to 229° C.

EXAMPLE 2

Synthesis of [D-(3-amino-3-carboxy)propyl-1]methylphosphinic acid

In 3 ml of tetrahydrofuran, 177 mg of potassium t-butoxide was dissolved under nitrogen stream and then the solution thus obtained was cooled to −78° C. To the solution, 200 mg of the compound (I)-2 ($R^1$=ethyl; absolute configuration=R) and further 190 mg of methyl ester of methyl vinylphosphinic acid were added. The resulting reaction mixture was stirred at −78° C. for 40 minutes and 2 ml of 1N HCl were added thereto, followed by concentration. To the residue thus obtained, 3 ml of 6N HCl was added and then the mixture was stirred under reflux for 20 hours. The reaction mixture was concentrated and 3 ml of propyleneoxide was added, followed by further stirring for 1 hour. After completion of stirring, the reaction mixture was concentrated and the crude product thus obtained was purified by use of an ion-exchange resin Dowex 50×2 (trade name, produced by Dow Chemical Co.) to give 92 mg (yield 64%) of crystalline powder of the desired product having a specific rotation of $[\alpha]_D$−12.4° (c=1.0, $H_2O$) and melting at 227° to 229° C.

EXAMPLE 3

Synthesis of [L-(3-amino-3-carboxy)propyl-1]methylphosphinic acid

In 6 ml of tetrahydrofran, 354 mg of potassium t-butoxide was dissolved under nitrogen stream and then the solution thus obtained was cooled to −78° C. To the solution, 377 mg of the compound (I)-1 ($R^1$=methyl; absolute configuration=S) and further 190 mg of methyl ester of methyl vinylphosphinic acid were added. The resulting reaction mixture was stirred at −78° C. for 30 minutes and 4 ml of 1N HCl were added thereto, followed by concentration.

The subsequent procedures were repeated in the same manner as in Example 1 to give 185 mg (yield 65%) of crystalline powder of the desired product having a specific rotation of $[\alpha]_D$+12.5° (c=1.0, H$_2$O) and melting at 227° to 229° C.

EXAMPLE 4

Synthesis of [L-(3-amino-3-carboxy)propyl-1]methylphosphinic acid

In 6 ml of tetrahydrofran, 354 mg of potassium t-butoxide was dissolved under nitrogen stream and then the solution thus obtained was cooled to −78° C. To the solution, 475 mg of the compound (I)-1 ($R^1$=phenyl; absolute configuration=S) and further 190 mg of methyl ester of methyl vinylphosphinic acid were added. The resulting reaction mixture was stirred at −78° C. for 30 minutes and 4 ml of 1N HCl were added thereto, followed by concentration.

The subsequent procedures were repeated in the same manner as in Example 1 to give 186 mg (yield 65%) of crystalline powder of the desired product having a specific rotation of $[\alpha]_D$+12.1° (c=1.0, H$_2$O) and melting at 227° to 229° C.

EXAMPLE 5

Synthesis of [L-(3-amino-3-carboxy)propyl-1]methylphosphinic acid

In 6 ml of tetrahydrofran, 354 mg of potassium t-butoxide was dissolved under nitrogen stream and then the solution thus obtained was cooled to −78° C. To the solution, 497 mg of the compound (I)-1 ($R^1$=benzyl; absolute configuration=S) and further 190 mg of methyl ester of methyl vinylphosphinic acid were added. The resulting reaction mixture was stirred at −78° C. for 30 minutes and 4 ml of 1N HCl were added thereto, followed by concentration.

The subsequent procedures were repeated in the same manner as in Example 1 to give 186 mg (yield 65%) of crystalline powder of the desired product having a specific rotation of $[\alpha]_D$+12.2° (c=1.0, H$_2$O) and melting at 227° to 229° C.

EXAMPLE 6

Synthesis of [L-(3-amino-3-carboxy)propyl-1]methylphosphinic acid

In 6 ml of tetrahydrofran, 354 mg of potassium t-butoxide was dissolved under nitrogen stream and then the solution thus obtained was cooled to −78° C. To the solution, 444 mg of the compound (I)-1 ($R^1$=t-butyl; absolute configuration=S) and further 190 mg of methyl ester of methyl vinylphosphinic acid were added. The resulting reaction mixture was stirred at −78° C. for 30 minutes and 4 ml of 1N HCl were added thereto, followed by concentration.

The subsequent procedures were repeated in the same manner as in Example 1 to give 184 mg (yield 64%) of crystalline powder of the desired product having a specific rotation of $[\alpha]_D$+12.4° (c=1.0, H$_2$O) and melting at 227° to 229° C.

EXAMPLE 7

Synthesis of [L-(3-amino-3-carboxy)propyl-1]ethylphosphinic acid

In 6 ml of tetrahydrofran, 354 mg of potassium t-butoxide was dissolved under nitrogen stream and then the solution thus obtained was cooled to −78° C. To the solution, 400 mg of the compound (I)-1 ($R^1$=ethyl; absolute configuration=S) and further 234 mg of ethyl ester of ethyl vinylphosphinic acid were added. The subsequent procedures were repeated in the same manner as in Example 1 to give 185 mg (yield 56%) of crystalline powder of the desired product having a specific rotation of $[\alpha]_D$+10.3° (c=1.0, H$_2$O) and melting at 183° to 186° C.

EXAMPLE 8

Synthesis of [L-(3-amino-3-carboxy)propyl-1]phenylphosphinic acid

In 6 ml of tetrahydrofran, 354 mg of potassium t-butoxide was dissolved under nitrogen stream and then the solution thus obtained was cooled to −78° C. To the solution, 400 mg of the compound (I)-1 ($R^1$=ethyl; absolute configuration=S) and further 309 mg of ethyl ester of phenyl vinylphosphinic acid were added. The subsequent procedures were repeated in the same manner as in Example 1 to give 235 mg (yield 58%) of crystalline powder of the desired product having a specific rotation of $[\alpha]_D$+7.3° (c=1.0, H$_2$O) and melting at 233° to 236° C.

EXAMPLE 9

Synthesis of [D-(3-amino-3-carboxy)propyl-1]methylphosphinic acid

In 3 ml of tetrahydrofran, 177 mg of potassium t-butoxide was dissolved under nitrogen stream and then the solution thus obtained was cooled to −20° C. To the solution, 200 mg of the compound (I)-1 ($R^1$=ethyl; absolute configuration=S) and further 95 mg of methyl ester of methyl vinylphosphinic acid were added. The resulting reaction mixture was stirred at −20° C. for 40 minutes and 2 ml of 1N HCl were added thereto, followed by concentration. To the residue thus obtained, 3 ml of 6N HCl was added and then the mixture was stirred under reflux for 20 hours. The reaction mixture was concentrated and 3 ml of propyleneoxide was added, followed by further stirring for 1 hour. One hour thereafter, the reaction mixture was concentrated and the crude product thus obtained was purified by use of an ion-exchange resin Dowex 50×2 (trade name, produced by Dow Chemical Co.) to give 62 mg (yield 43%) of crystalline powder of the desired product having a specific rotation of $[\alpha]_D$−11.5° (c=1.0, H$_2$O) and melting at 227° to 229° C.

EXAMPLE 10

Synthesis of [D-(3-amino-3-carboxy)propyl-1]methylphosphinic acid

In 3 ml of tetrahydrofran, 177 mg of potassium t-butoxide was dissolved under nitrogen stream and then the solution thus obtained was cooled to 0° C. To the solution, 200 mg of the compound (I)-1 ($R^1$=ethyl; absolute configuration=S) and further 95 mg of methyl ester of methyl vinylphosphinic acid were added. The resulting reaction mixture was stirred at 0° C. for 40 minutes and 2 ml of 1N HCl were added thereto, followed by concentration.

The subsequent procedures were repeated in the same manner as in Example 1 to give 35 mg (yield 24%) of crystalline powder of the desired product having a specific rotation of $[\alpha]_D -11.7°$ (c=1.0, H$_2$O) and melting at 227° to 229° C.

EXAMPLE 11

Synthesis of [L-(3-amino-3-carboxy)propyl-1]methylphosphinic acid

In 3 ml of tetrahydrofran, 177 mg of potassium t-butoxide was dissolved under nitrogen stream and then the solution thus obtained was cooled to −20° C. To the solution, 200 mg of the compound (I)-1 (R$^1$=ethyl; absolute configuration=R) and further 95 mg of methyl ester of methyl vinylphosphinic acid were added. The resulting reaction mixture was stirred at −20° C. for 40 minutes and 2 ml of 1N HCl were added thereto, followed by concentration.

The subsequent procedures were repeated in the same manner as in Example 1 to give 60 mg (yield 42%) of crystalline powder of the desired product having a specific rotation of $[\alpha]_D +10.6°$ (c=1.0, H$_2$O) and melting at 227° to 229° C.

EXPERIMENT 1

Barnyardgrass (*Echinochloa utilis ohwi*) seeds were sown into 6 cm diameter plastic pots packed with plowed soil, by sowing 8 to 9 grains per pot, and grown to 40 to 45 cm in grass height. At this stage, the predetermined amount of [L-(3-amino-3-carboxy)propyl-1]methylphosphinic acid (hereinafter Compound A: a compound prepared according to Example 1) or [DL-(3-amino-3-carboxy)propyl-1]methylphosphinic acid (hereinafter Compound B) was spread over the whole leaves of the barnyardgrass for treatment. Examination of herbicidal effects was carried out 14 days after the treatment. Estimation of the herbicidal effects was made in accordance with the standard shown in Table 1 based on the "Standard for Examination of Herbicides" by Japan Association for Advancement of Phytoregulators, Tokyo, 1975 and was indicated in terms of killing effect (%). Effect ratio of Compound A to Compound B and 95% reliability limit of the former were calculated from the killing effect thus obtained. Statistic calculations were in accordance with "D. Colquhorn in LECTURES ON BIOSTATISTICS, Oxford University Press, 1971". Results are shown in Table 2.

TABLE 1

| Standard for estimation of herbicidal activity | |
|---|---|
| Estimation index | Killing effect (%) |
| 0 | 0 |
| 1 | 10 |
| 2 | 20 |
| 3 | 30 |
| 4 | 40 |
| 5 | 50 |
| 6 | 60 |
| 7 | 70 |
| 8 | 80 |
| 9 | 90 |
| 10 | 100 |

TABLE 2

| Killing effect and effect ratio of Compound A to Compound B | | | | | |
|---|---|---|---|---|---|
| | Killing effect (%)* Amount of compound (g/are) | | | | |
| Compound | 1.25 | 2.5 | 5.0 | 10.0 | Effect ratio |
| Compound A | 45% | 52.5% | 64.2% | — | 2.05 (149–2.82)** |
| Compound B | 20.0% | 41.7% | 56.7% | — | 1 |

*Average of six replications
**95% Reliability limit

We claim:

1. A process for preparing optically active [(3-amino-3-carboxy)propyl-1]phosphinic acid derivatives, which comprises reacting a compound represented by the formula (I)-1:

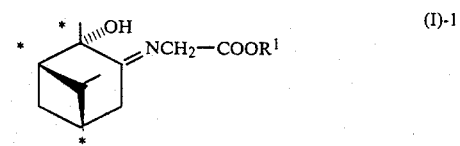

wherein R$^1$ represents a straight or branched chain alkyl group having 1 to 5 carbon atoms, an aryl group or an aralkyl group; and the absolute configurations of the three asymmetric carbon atoms indicated by * are each S-form or a compound represented by the formula (I)-2:

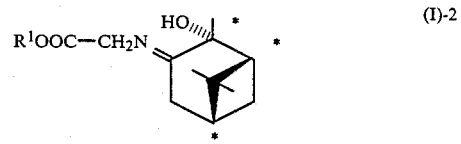

wherein R$^1$ have the same meaning as defined above; and the absolute configurations of the three asymmetric carbon atoms indicated by * are each R-form with a compound represented by the formula (II):

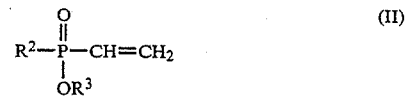

wherein R$^2$ and R$^3$ may be the same or different and each represent a straight or branched chain alkyl group having 1 to 5 carbon atoms, an aryl group or an aralkyl group, in the presence of a base, and subjecting the resulting compound to hydrolysis to form the optically active [L-(3-amino-3-carboxy)propyl-1]phosphinic acid derivatives represented by the formula (III)-1:

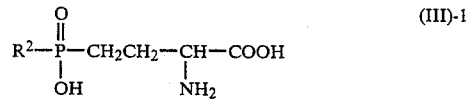

wherein R$^2$ have the same meaning as defined above; and the absolute configuration of the amino acid is L-form or [D-(3-amino-3-carboxy)propyl-1]phosphinic acid derivatives represented by the formula (III)-2:

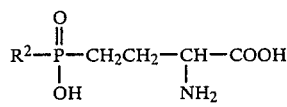

wherein $R^2$ have the same meaning as defined above; and the absolute configuration of the amino acid is D-form.

2. The process according to claim 1, wherein the compound of the formula (I)-1 or (I)-2 and the compound of the formula (II) is reacted at a temperature ranging from $-100°$ to 25° C.

3. The process according to claim 1, wherein the compound of the formula (II) is used in 1 to 2 moles per mole of the compound of the formula (I)-1 or (I)-2, and the base is used in 1 to 3 equivalent weights based on one equivalent weight of the compound of the formula (I)-1 or (I)-2.

4. The process according to claim 1, wherein the base is selected from the group consisting of n-butyl lithium, sec-butyl lithium, t-butyl lithium, lithium diisopropylamide, lithium isopropylcyclohexylamide, lithium di(trimethylsilyl)amide, sodium methylate, sodium ethylate, sodium hydride, potassium t-butoxide, calcium diisopropylamide, methylmagnesium chloride, methylmagnesium bromide and methylmagnesium iodide.

5. The process according to claim 1, which comprises reacting a compound represented by the formula (I)-1:

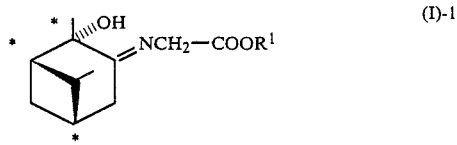

wherein $R^1$ represents a straight or branched chain alkyl group having 1 to 5 carbon atoms, an aryl group or an aralkyl group; and the absolute configurations of the three asymmetric carbon atoms indicated by * are each S-form with a compound represented by the formula (II):

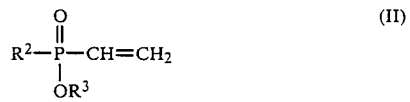

wherein $R^2$ and $R^3$ may be the same or different and each represent a straight or branched chain alkyl group having 1 to 5 carbon atoms, an aryl group or an aralkyl group, in the presence of a base, and subjecting the resulting compound to hydrolysis to form the optically active [L-(3-amino-3-carboxy)propyl-1]phosphinic acid derivatives represented by the formula (III)-1:

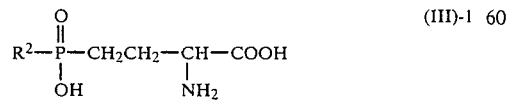

wherein $R^2$ have the same meaning as defined above; and the absolute configuration of the amino acid is L-form or [D-(3-amino-3-carboxy)propyl-1]phosphinic acid derivatives represented by the formula (III)-2:

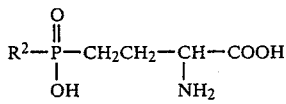

wherein $R^2$ have the same meaning as defined above; and the absolute configuration of the amino acid is D-form.

6. The process according to claim 5, wherein the compound of the formula (I)-1 and the compound of the formula (II) is reacted at a temperature ranging from $-100°$ to 25° C.

7. The process according to claim 6, wherein the compound of the formula (I)-1 and the compound of the formula (II) is reacted at a temperature ranging from $-100°$ to $-75°$ C. to form the optically active [L-(3-amino-3-carboxy)propyl-1]phosphinic acid derivatives represented by the formula (III)-1.

8. The process according to claim 6, wherein the compound of the formula (I)-1 and the compound of the formula (II) is reacted at a temperature ranging from $-60°$ to 25° C. to form the optically active [D-(3-amino-3-carboxy)propyl-1]phosphinic acid derivatives represented by the formula (III)-2.

9. The process according to claim 5, wherein the compound of the formula (II) is used in 1 to 2 moles per mole of the compound of the formula (I)-1, and the base is used in 1 to 3 equivalent weights based on one equivalent weight of the compound of the formula (I)-1.

10. The process according to claim 5, wherein the base is selected from the group consisting of n-butyl lithium, sec-butyl lithium, t-butyl lithium, lithium diisopropylamide, lithium isopropylcyclohexylamide, lithium di(trimethylsilyl)amide, sodium methylate, sodium ethylate, sodium hydride, potassium t-butoxide, calcium diisopropylamide, methylmagnesium chloride, methylmagnesium bromide and methylmagnesium iodide.

11. The process according to claim 1, which comprises reacting a compound represented by the formula (I)-2:

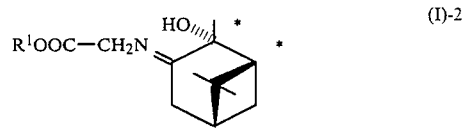

wherein $R^1$ represents a straight or branched chain alkyl group having 1 to 5 carbon atoms, an aryl group or an aralkyl group; and the absolute configurations of the three asymmetric carbon atoms indicated by * are each R-form with a compound represented by the formula (II):

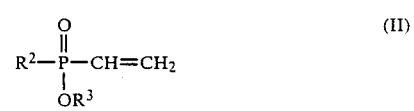

wherein $R^2$ and $R^3$ may be the same or different and each represent a straight or branched chain alkyl group having 1 to 5 carbon atoms, an aryl group or an aralkyl group,
in the presence of a base, and subjecting the resulting compound to hydrolysis to form the optically active

[L-(3-amino-3-carboxy)propyl-1]phosphinic acid derivatives represented by the formula (III)-1:

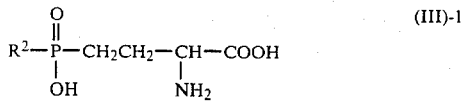     (III)-1 wherein R² have the same meaning as defined above; and the absolute configuration of the amino acid is L-form or [D-(3-amino-3-carboxy)propyl-1]phosphinic acid derivatives represented by the formula (III)-2:

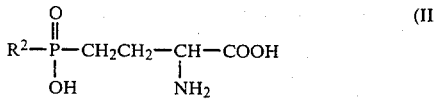     (III)-2 wherein R² have the same meaning as defined above; and the absolute configuration of the amino acid is D-form.

12. The process according to claim 11, wherein the compound of the formula (I)-2 and the compound of the formula (II) is reacted at a temperature ranging from −100° to 25° C.

13. The process according to claim 12, wherein the compound of the formula (I)-2 and the compound of the formula (II) is reacted at a temperature ranging from −100° to −75° C. to form the optically active [D-(3-amino-3-carboxy)propyl-1]phosphinic acid derivatives represented by the formula (III)-2.

14. The process according to claim 12, wherein the compound of the formula (I)-2 and the compound of the formula (II) is reacted at a temperature ranging from −60° to 25° C. to form the optically active [L-(3-amino-3-carboxy)propyl-1]phosphinic acid derivatives represented by the formula (III)-1.

15. The process according to claim 11, wherein the compound of the formula (II) is used in 1 to 2 moles per mole of the compound of the formula (I)-2, and the base is used in 1 to 3 equivalent weights based on one equivalent weight of the compound of the formula (I)-2.

16. The process according to claim 11, wherein the base is selected from the group consisting of n-butyl lithium, sec-butyl lithium, t-butyl lithium, lithium diisopropylamide, lithium isopropylcyclohexylamide, lithium di(trimethylsilyl)amide, sodium methylate, sodium ethylate, sodium hydride, potassium t-butoxide, calcium diisopropylamide, methylmagnesium chloride, methylmagnesium bromide and methylmagnesium iodide.

* * * * *